US012610112B2

(12) United States Patent
Hosemann

(10) Patent No.: US 12,610,112 B2
(45) Date of Patent: Apr. 21, 2026

(54) DETECTOR MODULE FOR AN X-RAY DETECTOR WITH A RADIO MODULE

(71) Applicant: Siemens Healthineers AG, Forchheim (DE)

(72) Inventor: Michael Hosemann, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 287 days.

(21) Appl. No.: 18/519,692

(22) Filed: Nov. 27, 2023

(65) Prior Publication Data

US 2024/0223875 A1      Jul. 4, 2024

(30) Foreign Application Priority Data

Dec. 30, 2022     (EP) ..................................... 22217299

(51) Int. Cl.
| | |
|---|---|
| *H04N 23/30* | (2023.01) |
| *A61B 6/03* | (2006.01) |
| *A61B 6/42* | (2024.01) |
| *G01T 1/20* | (2006.01) |
| *G01T 1/24* | (2006.01) |

(52) U.S. Cl.
CPC ............. *H04N 23/30* (2023.01); *A61B 6/032* (2013.01); *A61B 6/4233* (2013.01); *A61B 6/4291* (2013.01); *G01T 1/20182* (2020.05); *G01T 1/24* (2013.01)

(58) Field of Classification Search
CPC ...... H04N 23/30; A61B 6/032; A61B 6/4233; A61B 6/4291; G01T 1/20182; G01T 1/24
See application file for complete search history.

(56) References Cited

U.S. PATENT DOCUMENTS

| | | | |
|---|---|---|---|
| 9,606,245 B1 | 3/2017 | Czarnecki | |
| 2008/0272296 A1* | 11/2008 | Frach ........................ | A61B 6/56 |
| | | | 250/306 |
| 2010/0096556 A1 | 4/2010 | Arsalan | |
| 2011/0218432 A1 | 9/2011 | Tumer | |
| 2014/0093038 A1 | 4/2014 | Thalhammer | |
| 2016/0235387 A1* | 8/2016 | Murray .................... | A61B 6/56 |
| 2016/0256129 A1 | 9/2016 | Ergler | |
| 2020/0170593 A1 | 6/2020 | Ergler | |

FOREIGN PATENT DOCUMENTS

| | | | | |
|---|---|---|---|---|
| DE | 102011013057 A1 | 9/2012 | | |
| DE | 102015203764 A1 | 9/2016 | | |
| EP | 2713182 A2 * | 4/2014 | .......... | G01T 1/2985 |

* cited by examiner

Primary Examiner — Edwin C Gunberg
Assistant Examiner — Richard O Toohey
(74) Attorney, Agent, or Firm — Lempia Summerfield Katz LLC

(57) ABSTRACT

A detector module for an X-ray detector includes: a sensor unit configured to convert incoming X-rays into electrical signals; at least one readout unit configured to read out the electrical signals from the sensor unit; a radio module with a radio circuit, which is configured to transmit the readout electrical signals by a wireless data transmission method; and an electronic unit arranged in a stacked arrangement with respect to the sensor unit having at least one electrically conductive connection for forwarding the readout electrical signals from the at least one readout unit to the radio module, wherein the radio circuit of the radio module is at least partially embedded in an embedding material of the electronic unit.

13 Claims, 5 Drawing Sheets

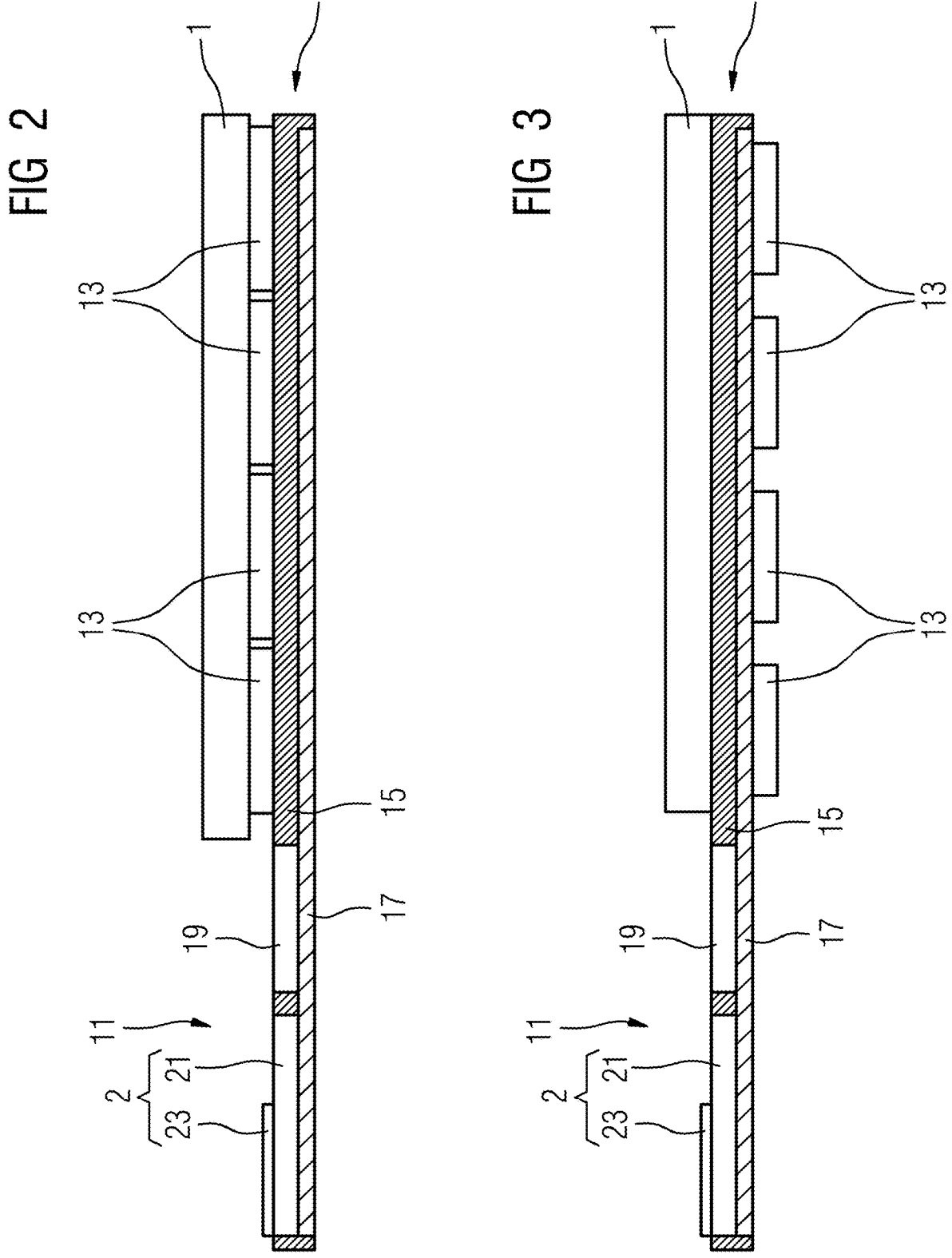

DETECTOR MODULE FOR AN X-RAY DETECTOR WITH A RADIO MODULE

The present patent document claims the benefit of European Patent Application No. 22217299.1, filed Dec. 30, 2022, which is hereby incorporated by reference in its entirety.

TECHNICAL FIELD

The disclosure relates to a detector module for an X-ray detector having a sensor unit, at least one readout unit, and at least one electronic unit arranged in a stacked arrangement with respect to the sensor unit including a radio module with a radio circuit, wherein the radio circuit of the radio module is at least partially embedded in an embedding material of the electronic unit. The disclosure further relates to an X-ray detector and a medical imaging device including such a detector module.

BACKGROUND

X-ray detectors are used in many imaging applications. For example, X-ray detectors are used in computed tomography systems (CT systems) in medical imaging to generate a tomographic X-ray image of an area under examination.

CT systems are well known. It is also generally known that large amounts of data are generated in the rotating part of a CT system, which is transmitted to the stationary part. In particular, the detector data generated in one or more detectors rotating around the system axis of the CT system is transmitted promptly for evaluation.

Currently, data transmission may be carried out using slip ring systems, which establish a data transmission path via a capacitive coupling between the rotating and stationary parts. However, this technology may reach its limits if the amount of data to be transmitted continues to increase in the future as detectors are further developed. For example, the data transmission requirements of counting detectors, which have a much finer pixelation and also have several energy thresholds per pixel, further swelling the amount of data to be transmitted, have increased significantly compared to conventional detectors. Furthermore, such a slip ring system may be susceptible to performance losses due to wear and contamination.

It is generally known that consideration has been given, for the transmission of detector data between a rotating detector and a stationary part of the CT system or a receiver in the application room, to using radio transmission links, e.g., a wireless data transmission method, instead of slip ring systems. Apart from advantages in the transmission of large amounts of data, the implementation of data transmission by radio transmission may reduce costs for maintenance and renewal of systems compared to implementation by slip rings. When providing a detector that enables such wireless transmission of detector data, a cost-efficient and easy-to-use implementation is desirable.

SUMMARY AND DESCRIPTION

The object of the disclosure is to provide an improved detector module for an X-ray detector that enables data transmission by a wireless data transmission method.

The scope of the present disclosure is defined solely by the appended claims and is not affected to any degree by the statements within this summary. The present embodiments may obviate one or more of the drawbacks or limitations in the related art.

The disclosure relates to a detector module for an X-ray detector including: a sensor unit configured to convert incoming X-rays into electrical signals; at least one readout unit configured to read out the electrical signals from the sensor unit; a radio module with a radio circuit which is configured to transmit the readout electrical signals by a wireless data transmission method; and an electronic unit arranged in a stacked arrangement with respect to the sensor unit and having at least one electrically conductive connection for forwarding the readout electrical signals from the at least one readout unit to the radio module, wherein the radio circuit of the radio module is at least partially embedded in an embedding material of the electronic unit.

The sensor unit may include a direct-converting or an indirect-converting converter material. The X-rays or X-ray photons may be converted into electrical signals in direct-converting sensor units using a suitable converter material. For example, CdTe, CZT, CdZnTeSe, CdTeSe, CdMnTe, InP, TlBr$_2$, HgI$_2$, GaAs, or others may be used as converter material. The X-rays or photons may be converted into light in indirect-converting sensor units using a suitable converter material and into electrical pulses by optically coupled photodiodes, e.g., a photodiode array. Scintillators, (e.g., GOS (Gd$_2$O$_2$S), CsJ, YGO or LuTAG), may be used as the converter material. In particular, the sensor unit may have a planar extension along two directions perpendicular to the stacking direction of the stacking arrangement. The sensor unit may have a one-piece converter element or be composed of a plurality of these positioned next to one another along the planar extension.

In both types, the radiation detector module may include a large number of pixel elements, e.g., the smallest flat areas that may be read out independently. In order to be read out, each pixel is connected to an associated evaluation pixel element of a readout unit. There may be one readout unit or a plurality of readout units in the detector module, which are assigned to the sensor unit. A readout unit may be used to digitize the electrical signals that are fed into the sensor unit. A readout unit may be implemented as an Application Specific Integrated Circuit (ASIC).

According to the disclosure, the sensor unit is present in a stacked arrangement with the electronic unit. The stacking direction of the stacking arrangement runs parallel to a beam incidence direction of X-rays for exposing an X-ray detector when the detector module is used. In the stacking arrangement, the sensor unit faces the incident radiation, with the electronic unit coming after the sensor unit in the beam incidence direction. In the stack arrangement, the electronic unit has a planar extension that extends parallel to the planar extension of the sensor unit. In particular, the electronic unit may have at least the same planar extent as the sensor unit. In other embodiments, several sensor units may be assigned to a common electronic unit, or the electronic unit may extend beyond the planar extent of the sensor unit or the sensor units and have a larger planar extension. It cannot be excluded that further elements may be present in a stacked arrangement between the electronic unit and the sensor unit. Nor may it be excluded that the stacking arrangement includes further elements that may be located upstream or downstream along the stacking direction and in a stacking arrangement. For example, this may involve an anti-scatter grid, a module carrier, a heat sink, or another unit necessary for the operation of the detector module.

The at least one readout unit or the plurality of readout units may also be present in a stacked arrangement with the sensor unit. The at least one readout unit or the multiple readout units also includes a planar extension that extends parallel to the planar extension of the sensor unit in the stacking arrangement.

The at least one readout unit or the several readout units may be arranged directly adjacent to the sensor unit and connected to the sensor unit, (e.g., via bump bonds or a conductive adhesive connection), for signal transmission. In other examples, the readout unit(s) may also be connected to the sensor unit via one or more other elements, (e.g., an electronic unit arranged in between), by appropriately configured electrically conductive connections. Furthermore, according to one variant, the at least one readout unit may also be at least partially embedded in the embedding material of the electronic unit.

The electronic unit may include a non-conductive embedding material, in particular a polymer, (e.g., a plastic material or an epoxy resin), in which at least the radio circuit is at least partially embedded, and one or more electrically conductive connections, which are also embedded in the material or configured on a surface of the electronic unit.

At least one electrically conductive connection of the electronic unit serves to forward the electrical signals read out by the at least one readout unit and possibly preprocessed by the readout unit, (also known as detector data), to the radio module. In particular, a plurality of electrically conductive connections may also be provided for this purpose. The at least one electrically conductive connection for signal transmission between the at least one readout unit and the radio module may be embedded in the embedding material of the electronic unit or applied to the embedding material of the electronic unit. Wiring may be applied lithographically, by a sputtering technique, a vapor phase deposition process, or by a line pressure process to a surface of the embedding material of the electronic unit. Furthermore, vias may be provided that enable electrically conductive connections through the embedding material.

Depending on the arrangement of the electronic unit or the readout unit in the stack arrangement, the electronic unit may have electrically conductive connections between the sensor unit and the readout unit. Furthermore, other electrically conductive connections may also be provided, e.g., for the supply of control signals to the readout unit or units or the radio module, or for the supply of an operating voltage. The electronic unit may also include further electronic assemblies arranged on or in the electronic unit and which are provided for the operation of the detector module.

The electronic unit may advantageously increase the stability and thus the manageability of the stacking arrangement. Furthermore, the electronic unit may enable the rewiring of contact points, (e.g., from the sensor unit to the readout unit or units), and thus advantageously different, possibly more cost-efficient, sizes or also the combination of data from several readout units before forwarding to the radio module.

The radio module is configured to send the detector data by a wireless data transmission method, e.g., by radio technology. The radio module as a transmitter may work together with a further radio module placed outside the X-ray detector as a receiver, so that the detector data may be transmitted from the detector module to the further receiver radio module placed outside the X-ray detector. There may also be embodiments in which the radio module of the detector module may also be configured as a receiver in order to receive radio signals, (e.g., including control signals for the detector module), from a transmitter placed outside the X-ray detector. In this way, control signals for the detector module may also be advantageously transmitted by wireless data transmission. Advantageously, further data transmission paths for control via a slip ring design may be avoided and cabling costs reduced. The transmitter may then be included in the same radio module that is also intended for receiving the detector data.

It is also possible for a detector module to include several radio modules, in which case the detector data for wireless data transmission is divided between the several radio modules.

The radio module has at least one radio circuit and a radio antenna. In certain examples, the radio module may include at least one radio circuit in the form of an integrated circuit (IC), also known as a solid-state circuit. In particular, this may be configured as an ASIC (application-specific integrated circuit). In advantageous embodiments, the radio antenna may be configured as an antenna array.

The radio circuit, together with the radio antenna, is configured to send the detector data, which is forwarded from the readout unit(s) to the radio module, by a wireless data transmission method, e.g., to transmit the data to a receiver unit. The method of wireless data transmission or the implementation of antennas is selected in particular in such a way that it is suitable for the data transmission of the detector data and is in particular also to be configured to the specific embodiment and the specific use of the detector module. An X-ray detector in a CT system may thus have different requirements in terms of data volume and existing interference signals, for example, than in another medical device. The positioning of the transmitter relative to the receiver is also considered. An arrangement of a receiver in the stationary part of a CT system, in particular, in the direct vicinity of the rotor may enable a different implementation than the provision of a receiver at a location outside the CT device, (e.g., separately in the application room), due to a significantly smaller distance between a radio module of the detector module and the receiver. A wireless data transmission method may use a WLAN (wireless local area network) standard, which may use frequency bands in the 2.4 GHz or 5 GHz range. However, other implementations may also be provided, in particular those that are optimized for shorter distances between the transmitter and receiver, if the arrangement in the application device, (e.g., in the CT system), allows this.

The radio circuit of the radio module is at least partially embedded in the embedding material of the electronic unit. As already described above, the electronic unit consequently includes at least the radio circuit embedded in the embedding material of the electronic unit as well as corresponding electrically conductive connections and, if necessary, contacts that are integrated into the electronic unit or applied to a surface in order to enable signal transmission to the radio circuit. This may advantageously increase the robustness of the assembly and increase protection against damage to the components. It is also advantageous to use manufacturing processes for the electronic unit with the radio circuit that rely on the use of what are known as "bare dies" for the radio circuit, which may be particularly cost-effective. Furthermore, a very compact assembly with small dimensions may be advantageously achieved, which may facilitate mounting of the detector module. In particular, the radio circuit may be at least partially embedded at least on three sides. It may also be completely embedded in the embedding material.

In particular, the electronic unit may be manufactured using what are known as wafer-level packaging methods, in which chips are embedded in polymer encapsulations, e.g., a fan-out wafer-level packaging method, or panel-level packaging methods. Advantageously, a large number of electronic units with radio circuits already integrated may be provided in a cost-effective and parallelized manner. In this case, the electronic unit thus forms an assembly that includes the radio circuit, the housing surrounding the electronic unit and, if necessary, electrically conductive connections for contacting. Due to the larger number of chips that may be processed in parallel, panel-level packaging methods enable a further increase in productivity and lower package costs resulting therefrom. The methods also offer the advantage of a very thin package, low thermal resistance, and low interference and inductances owing to short electrical connections. An alternative variant includes PCB (printed circuit board) embedding methods, in which the chips are embedded in PCB material.

In alternative embodiments of a detector module, the radio circuit is only arranged on the electronic unit.

It is advantageous to equip the detector module directly with a radio unit so that the detector data may be transferred to the radio unit in the immediate vicinity of their point of origin and the transmission may take place. The transmission paths and intermediate acts are advantageously short. Due to the integration of the radio module into the stack arrangement, the necessary assemblies and cabling effort may be advantageously reduced. A further advantage is that the radio transmission technology is also widely used outside of X-ray detectors or computed tomography and therefore offers significantly more cost-effective assemblies than, for example, when using slip ring technology. Advantageously, the stacking arrangement provides an extremely robust assembly that is easy to handle and therefore cost-efficient to install.

According to an advantageous variant, the at least one readout unit and the radio circuit are at least partially embedded in the embedding material of the electronic unit, in particular at least partially from three sides or completely. Advantageously, this may increase the protection against damage to the readout units, and an extremely compact assembly may also be provided, which avoids the additional space usage caused by a separately mounted readout unit. As with the radio circuit, it is also possible to use manufacturing processes that allow a high degree of parallelization in the provision or that rely, for example, on the use of "bare dies" for the circuit, which may be particularly cost-effective.

According to an advantageous embodiment, the electronic unit has a surface area that protrudes in a direction perpendicular to the stacking direction beyond the planar extension of the sensor unit, wherein the radio module is arranged in the protruding surface area. Advantageously, wireless data transmission is not disturbed by the sensor unit or other components of the detector module. In an advantageous manner, it may also be avoided that the radio circuit causes a heat input into the sensor unit which may result in a loss of image quality.

According to an advantageous embodiment, the radio module has at least one radio antenna, which includes a wire applied to a surface of the embedding material of the electronic unit or to a surface of the radio circuit. This may be applied lithographically, by a sputtering technique, or by a line pressure process. Advantageously, lithographic application allows particularly precise and extremely fine structuring. In particular, the provision of the antenna may already be applied during the manufacture of the electronic unit, e.g., as part of a packaging process. Advantageously, a cost-effective provision may be made possible whereby additional components may also be dispensed with. In particular, this represents an advantageously robust and compact implementation. Advantageously, the electronic unit provides an assembly in which the components for wireless data transmission and their contacting are integrated.

According to a further embodiment variant, the detector module may also have a separate control circuit configured to control the at least one readout unit and/or the radio module. In an alternative embodiment, the radio circuit and the control circuit, which allows the radio circuit to be controlled, are an integrated assembly. However, this requires a targeted design and therefore an application-specific embodiment. By designing the control circuit and the radio circuit separately, it is easier to use more cost-effective, easy-to-obtain standard assemblies. Furthermore, the control circuit may also be configured to control the readout units. This may include only controlling the readout process. But it may also include, for example, controlling a configuration of the readout units for the measuring process. The control circuit may also be configured as an ASIC. In advantageously favorable variants, the control circuit may be configured as an FPGA (field programmable gate array). This may also allow a more flexible adaptation of the control circuit, as repeated programming of the functionalities of the control circuit is possible here.

According to an embodiment variant thereof, the control circuit is also at least partially embedded in the embedding material of the electronic unit, so that a compact structure is advantageously provided. The advantages of the embedding are similar to the advantages of embedding the radio circuit or a readout unit. Advantageously, an integrated, compact, and robust assembly is provided.

According to one embodiment variant, the electronic unit is arranged in the stack arrangement, in particular between the sensor unit and the at least one readout unit. Advantageously, this enables a larger sensor unit to be rewired to one or more readout units with a smaller planar extension, which may be provided more cost-effectively. The same may also be advantageously achieved if the readout unit is embedded in the electronic unit and a corresponding rewiring layer is provided on or in the electronic unit.

As described above, the sensor unit may be configured as a direct-conversion sensor unit or include a scintillator element and at least one photodiode array, depending on the embodiment variant. In particular when using direct-conversion sensor units, a very large amount of data may be generated, which may be advantageously transmitted in an improved manner at a high data rate using an implementation that includes wireless data transmission by a radio module. However, such an implementation may also be advantageous with scintillator-based implementations because the disadvantages of a slip ring-based implementation may be avoided.

The disclosure further relates to an X-ray detector including a plurality of detector modules according to one of the preceding claims. The plurality of detector modules may be arranged next to each other in the X-ray detector, so that the sensor units together act as a larger detection surface.

Advantageously, each detector module has a radio module so that the detector data generated in a detector module may be transferred directly to the respective radio unit present in this detector module and transmitted directly without any further intermediate acts or paths. In this way, transmission of the data over longer data transmission paths to a sender unit is also avoided. Furthermore, parallel data transmission of the detector data from the modules may enable a particularly high data transmission rate overall. Furthermore, this allows detectors with different numbers of modules to be produced without significant effort in the development of electronic hardware.

It would also be conceivable for an X-ray detector to combine detector modules with a radio module and those without a radio module, whereby a feed of the detector data from such modules without a radio module to those with a radio module is provided. For example, these may be arranged alternately next to each other. Although this increases the amount of data to be transmitted by a radio module, it may at least partially save costs as a radio module does not have to be provided in every detector module.

All embodiment variants previously described in the context of the detector module may accordingly also be implemented in the X-ray detector. The description given with regard to the detector module and the advantages of the detector module described above may accordingly also be transferred to the X-ray detector.

The X-ray detector may also have other components, such as a housing that at least partially encloses the modules.

The disclosure further relates to a medical imaging device including a detector module or an X-ray detector according to one of the variants described above.

In contrast to the detector module or the X-ray detector including such a detector module, the medical imaging device includes an X-ray source configured to expose the detector module or the X-ray detector to X-rays along the beam incidence direction.

To record the X-ray image data set, an object to be imaged may be placed between the X-ray source and the detector module or X-ray detector and irradiated by the X-ray source.

In particular, the medical imaging device may be configured as a computed tomography system. However, it may also be configured, for example, as a C-arm X-ray device and/or Dyna-CT or as another X-ray-based imaging device.

All embodiment variants previously described in the context of the detector module or X-ray detector may also be implemented accordingly in the medical imaging device. The description given with regard to the detector module or the X-ray detector and the advantages described above may accordingly also be transferred to the medical imaging device.

According to one embodiment variant, the medical imaging device is configured as a computed tomography device, wherein the at least one detector module or the X-ray detector is arranged on the rotating part and at least one receiver unit, which interacts with the radio module for data transmission, is arranged on a stationary part of the computed tomography device.

The receiver unit includes at least one antenna that allows the detector data transmitted by the radio module to be received and a circuit that allows the detector data to be processed and forwarded. The receiver unit and the radio module work together during wireless data transmission and are coordinated with each other so that data transmission is enabled. Placing the receiver unit on the stationary part of the CT device is advantageous, as this allows a relatively small and also defined distance to be covered for data transmission. An arrangement outside the CT device firstly involves greater transmission distances and secondly possibly different conditions from application to application, which is considered.

According to one embodiment variant of the computed tomography device described above, the imaging device includes a plurality of receiver units. This may allow parallel data transmission to the plurality of receiver units. Furthermore, it is also conceivable that the receiver unit is advantageously used in each case for transmission, which receiver unit is optimally positioned in relation to a radio module for radio transmission.

Furthermore, the receiver units may be mounted on the stator in different arrangements in order to achieve optimum and/or alternating reception situations. Examples of this are a ring-shaped arrangement on the stationary part around an axis of rotation of the computed tomography device or an arrangement as a group on the stator.

Within the scope of the disclosure, features which are described in relation to different may also be combined to form further embodiments. In addition to the embodiments expressly described in this application, other embodiments of the disclosure are conceivable, at which the person skilled in the art may arrive without leaving the scope of the disclosure, which is predetermined by the claims.

The use of the indefinite article "a" does not exclude the possibility that the characteristic concerned may be present more than once. The use of the term "having" does not exclude that the terms linked by the term "having" may be identical. For example, the medical imaging device has the medical imaging device. The use of the term "unit" does not exclude that the object to which the term "unit" refers may include several components that are spatially separated from each other.

In the following, the disclosure is explained by embodiments with reference to the attached figures. The illustration in the figures is schematic, highly simplified, and not necessarily true to scale.

BRIEF DESCRIPTION OF THE DRAWINGS

FIG. 2 to FIG. 5 depict detailed views of a stack arrangement of a detector module according to different examples.

DETAILED DESCRIPTION

Figure 1:
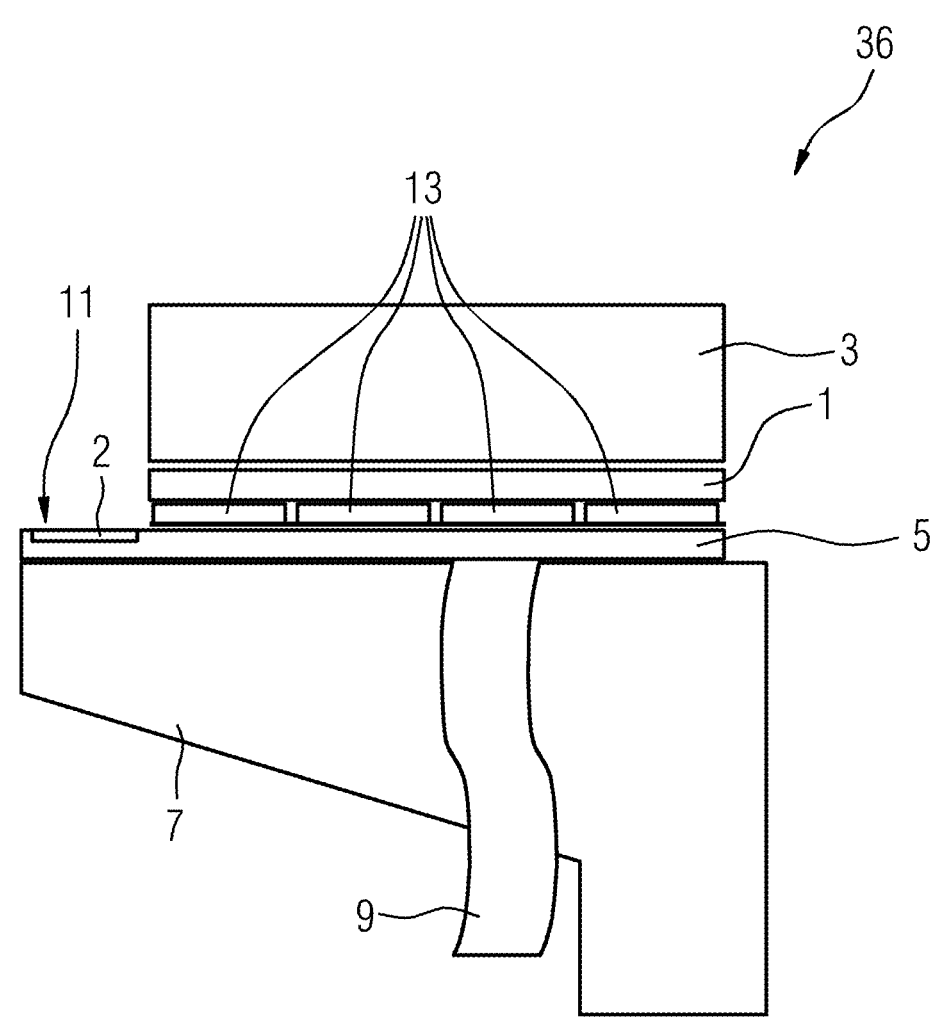
FIG. 1 depicts a schematic cross-section of an example of a detector module.

FIG. 1 shows a schematic cross-section of a detector module according to an embodiment.

The detector module has a sensor unit 1 configured to convert incoming X-rays into electrical signals. Furthermore, the detector module has at least one readout unit 13 configured to read out the electrical signals from the sensor unit 1. In the variant shown, the detector module has at least four readout units 13. However, there may also be a different number, (e.g. 8 or even just one). Furthermore, the detector module has a radio module 2 with a radio circuit 21, which is configured to send the readout electrical signals by a wireless data transmission method. Furthermore, the detector module has an electronic unit 5 arranged in a stacked arrangement with respect to the sensor unit 1, wherein the radio circuit 21 of the radio module 2 is at least partially embedded in an embedding material of the electronic unit 5. Not explicitly shown here, the at least one electrically conductive connection 17 is configured to forward the readout electrical signals from the at least one readout unit 13 to the radio module 2, which has the electronic unit 5.

The sensor unit may be configured as a direct-converting sensor unit including a suitable converter material such as CdTe, CZT, CdZnTeSe, CdTeSe, CdMnTe, InP, TlBr$_2$, HgI$_2$, or GaAs. Alternatively, the sensor unit 1 includes an indirect-converting converter material 25, (e.g., a scintillator), and at least one photodiode array 29 coupled thereto.

The sensor unit 1 is arranged in a stacked arrangement with the electronic unit 5. In the embodiment shown here, the readout units 13 are also arranged in a stacked arrangement between the sensor unit 1 and the electronic unit 5 and directly adjacent to the sensor unit and connected to the sensor unit, (e.g., via bump bonds or a conductive adhesive connection), for signal transmission. However, other arrangements are possible. In particular, the electronic unit 5 may also be arranged between the readout units 13 and the sensor unit 1, wherein the readout units are then connected to the sensor unit 1 by electrically conductive connections configured in the electronic unit 5. In a further alternative embodiment, the readout units 13 may also be embedded in the embedding material 15 of the electronic unit 5. The readout units 13 may be configured as ASICs.

The electronic unit 5 may include a non-conductive embedding material, in particular a polymer, (e.g., a plastic material or an epoxy resin), and one or more electrically conductive connections embedded in the embedding material or configured on a surface of the embedding material. In addition, the radio circuit of the radio module 2, including at least the radio circuit and a radio antenna or a radio antenna array (see also the following figures), is embedded in the embedding material of the electronic unit 5. The radio module 2 is configured to send the detector data by a wireless data transmission method, e.g., by radio technology. The radio module as a transmitter may work together with a further radio module placed outside the X-ray detector as a receiver, so that the detector data may be transmitted from the detector module to the further receiver radio module placed outside the X-ray detector. There may also be embodiments in which the radio module 2 of the detector module may also be configured as a receiver in order to receive radio signals, (e.g., including control signals for the detector module), from a transmitter placed outside the X-ray detector.

In particular, the electronic unit 5 with the radio circuit may be manufactured particularly advantageously using what are known as wafer-level packaging methods, e.g., a fan-out wafer-level packaging method, or panel-level packaging methods. Advantageously, a large number of electronic units with radio circuits already integrated may be provided in a cost-effective and parallelized manner.

According to an advantageous embodiment, the electronic unit 5 also has a surface area that protrudes in a direction perpendicular to the stacking direction of the stacking arrangement beyond the planar extension of the sensor unit, wherein the radio module 2 is arranged in the protruding surface area. Advantageously, wireless data transmission is not disturbed by the sensor unit or other components of the detector module. In an advantageous manner, it may also be avoided that the radio circuit causes a heat input into the sensor unit which may result in a loss of image quality.

In the variant shown here, the detector module has further components, such as a carrier unit 7, which may also act as a heat sink. An anti-scatter grid 3 is also provided, which is arranged in front of the sensor unit in the beam incidence direction. Electrical lines 9 are also provided here, which may supply an operating voltage or, if not transmitted by radio, control signals for the readout units or for the radio module 2.

FIG. 2 to FIG. 5 show detailed views of a stack arrangement of a detector module according to different embodiment variants.

As in FIG. 1, FIG. 2 shows the evaluation units 13 in a stacked arrangement and arranged next to the sensor unit 1. The evaluation units 13 are therefore located in the stacked arrangement between the sensor unit 1 and the electronics unit 5. Furthermore, a rewiring layer 17 is integrated into the embedding material 15 of the electronic unit 5, which realizes the electrically conductive connections between the units. The rewiring layer may be configured in such a way that wiring is formed on a substrate, which is molded together with the circuits to form the package of the electronic unit 5 through the embedding material. It may also be implemented differently. In addition to the wiring layer, further electrically conductive connections may also be configured in the vertical direction, which enable contacting of the readout units. The radio circuit may be configured as an ASIC, for example. The radio antenna 23 of the radio module 2 includes at least one wire applied to the surface of the electronic unit 5. This may be applied lithographically, by a sputtering technique, or by a line pressure process. The radio antenna 23 is advantageously configured as a radio antenna array.

According to a further embodiment variant, the detector module also includes a separate control circuit 19 configured to control the readout units 13 and the radio module 2. In advantageously favorable variants, the control circuit may be configured as an FPGA. However, there may also be other embodiment variants such as an ASIC. In particular, there may also be embodiments in which the control circuit 19 and the radio circuit 21 are implemented as a common circuit. Equally, control signals may still be transmitted via a cable provided for this purpose.

The control circuit 19 is also embedded here in the embedding material 15 of the electronic unit 5, so that a compact structure and an integrated package including radio module 2, control circuit 19, and corresponding wiring 17 is advantageously provided.

FIG. 3 shows the same units as in FIG. 2, but the arrangement of the readout units 13 is different. In this variant, the electronic unit 5 is arranged in the stack arrangement, in particular between the sensor unit 1 and the readout units 13. The electronic unit 5 then also has corresponding electrically conductive connections that connect the sensor unit 1 to the readout units 13. The electronic unit 5 serves here as what is known as an interposer and may realize a rewiring from an overall larger sensor surface of the sensor unit 1 to readout units 13 with smaller dimensions, which may be provided more cost-effectively.

Figures 4, 5:
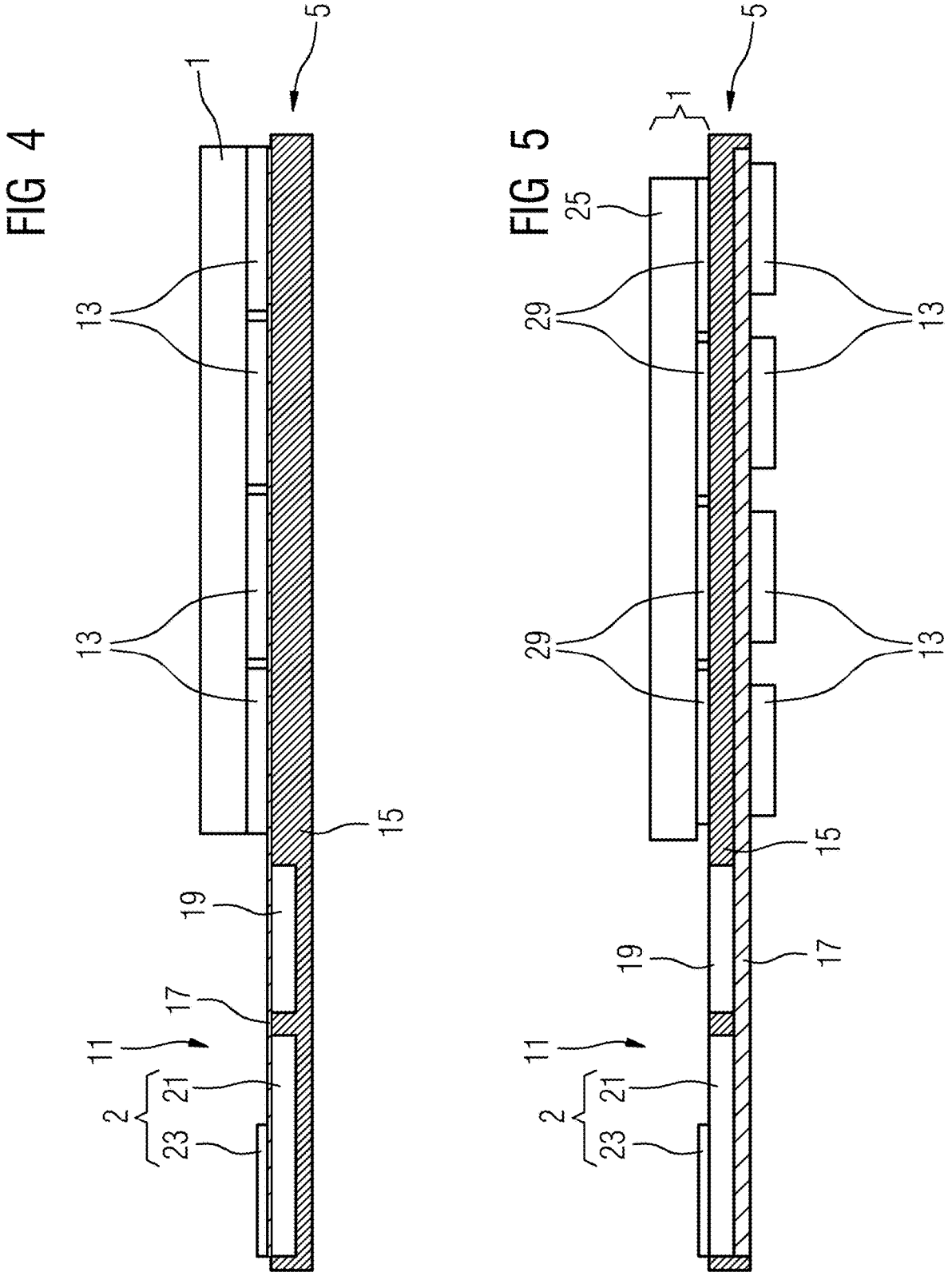

In contrast to FIG. 2, FIG. 4 does not show a rewiring layer integrated into the embedding material of the electronic unit, but rather a rewiring 17 applied to a surface, (e.g., lithographically), which connects the units of the detector module for signal transmission accordingly. This allows a further reduction in height to be achieved in variants.

In contrast to FIG. 2, FIG. 5 also explicitly shows the embodiment of the sensor unit 1 as an indirect-conversion sensor unit 1 including a scintillator 25 and photodiode arrays 29 coupled thereto.

Figure 6:
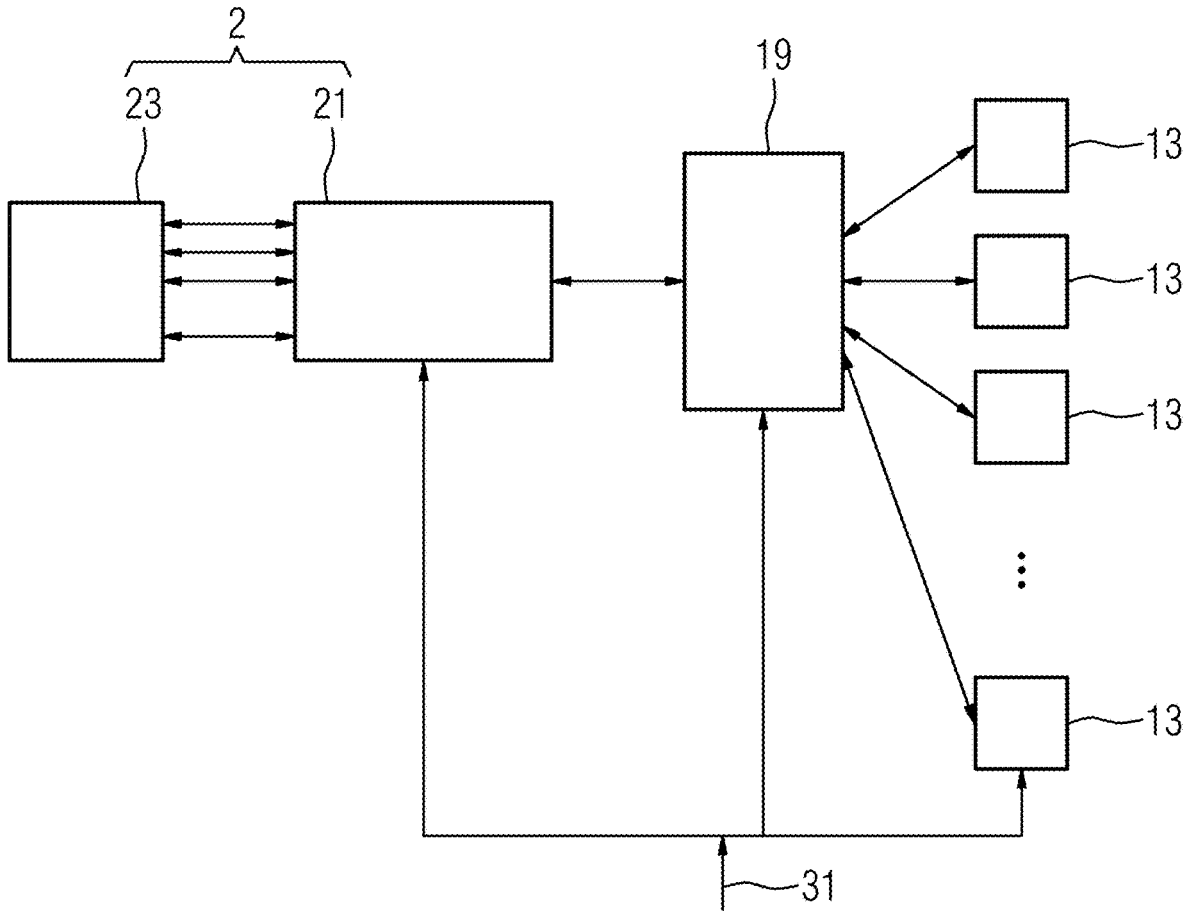
FIG. 6 depicts schematically an example of the interaction of individual components of the detector module.

FIG. 6 schematically shows once again the interaction of the individual components of the detector module.

The control circuit 19 is configured to control the readout units 13 at least for reading out the detector data and the radio circuit 21 of the radio module 2. An antenna array 23 is then used for data transmission, via which the detector data is sent to a correspondingly tuned receiver, which is arranged outside the detector. An operating voltage supply 31 is also provided for the operation of the readout units 13, the control circuit 19 and the radio circuit 21.

Figure 7:
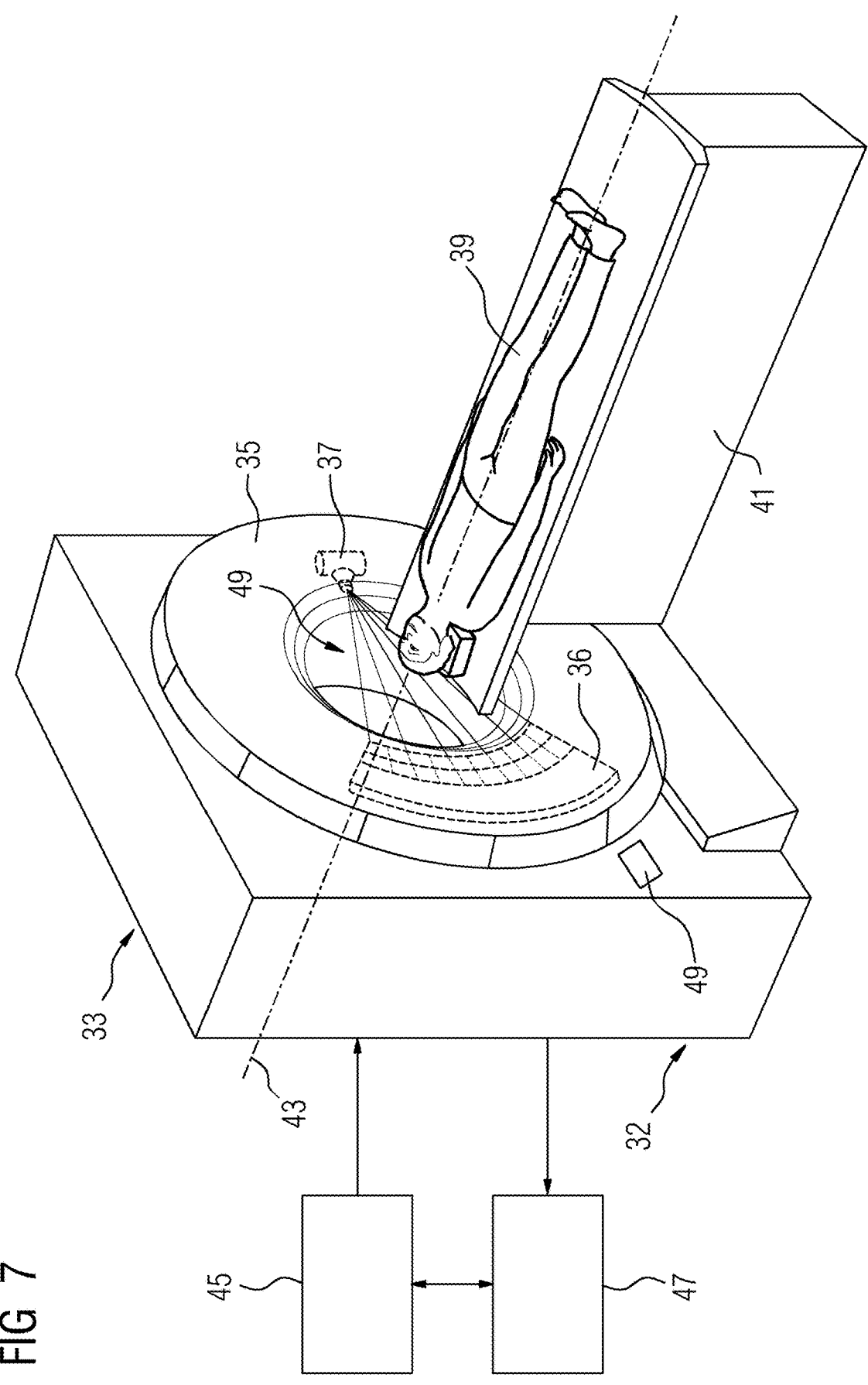
FIG. 7 depicts a schematic representation of an example of a medical imaging device.

FIG. 7 further shows an exemplary embodiment of a medical imaging device 32 with an X-ray detector 36 and an X-ray source 37 in opposition to the X-ray detector 36. The X-ray source 37 is configured to expose the X-ray detector 36 with X-rays along a beam incidence direction. The medical imaging device 32 shown is configured in particular as a CT device. The CT device includes a gantry 33 with a rotor 35. The rotor 35 includes the X-ray source 37 and the X-ray detector 36. The rotor 35 is rotatable about the axis of rotation 43. The object to be examined 39, (e.g., a patient), is supported on the patient couch 41 and may be moved along the axis of rotation 43 through the gantry 33. A computing unit 45 is used to control the computed tomography system and to calculate sectional images or volume images of the object. The computing unit 45 in the form of a computer system is configured to reconstruct X-ray image data based on the data from the X-ray detector 36 of the CT device. Another computer system serves as an operator console 47. The software installed on the operator console 47 enables the operator to control the operation of the CT device, such as selecting a protocol, starting scanning, etc. The operator console 47 may also be configured as a computer system.

In particular, the X-ray detector 36 includes a plurality of detector modules according to one of the variants described above, each including a radio module 2.

The plurality of detector modules may be arranged next to each other in the X-ray detector 36, so that the sensor units 1 together act as a larger detection surface. Advantageously, each detector module of the X-ray detector 36 has a radio module so that the detector data generated in a detector module may be transferred directly to the respective radio unit present in this detector module and transmitted directly without any further intermediate acts or paths. It would also be conceivable for an X-ray detector to combine detector modules with a radio module and those without a radio module, whereby a feed of the detector data from such modules without a radio module to those with a radio module is provided.

The CT device also has at least one receiver unit 49 on the stationary part, which acts together with the radio modules 2 for wireless data transmission.

The receiver unit 49 includes at least one receiver antenna that allows the detector data transmitted by a radio module 2 to be received and a circuit that allows the detector data to be processed and forwarded. Placing the receiver unit 49 on the stationary part of the CT device is advantageous, as this allows a relatively small and also defined distance to be covered for data transmission. An arrangement outside the CT device involves greater transmission distances and possibly different conditions from application to application, which is taken into account. However, such a placement is also possible.

In advantageous design variants, the CT device includes a plurality of receiver units 49. These may be mounted on the stator in different arrangements in order to achieve optimum and/or alternating reception situations. Examples of this are a ring-shaped arrangement on the stationary part around an axis of rotation of the CT device or an arrangement as a group on the stator.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A detector module for an X-ray detector, the detector module comprising:
   a sensor configured to convert incoming X-rays into electrical signals;
   at least one readout unit configured to read out the electrical signals from the sensor;
   a radio having a radio circuit, wherein the radio is configured to transmit the readout electrical signals by a wireless data transmission method; and
   an electronic unit arranged in a stacked arrangement with respect to the sensor, wherein the electronic unit comprises at least one electrically conductive connection for forwarding the readout electrical signals from the at least one readout unit to the radio,
   wherein the radio circuit of the radio is at least partially embedded in an embedding material of the electronic unit,
   wherein the electronic unit has a protruding surface area that protrudes in a direction perpendicular to a stacking direction beyond a planar extension of the sensor, and
   wherein the radio is arranged in the protruding surface area.

2. The detector module of claim 1, wherein the at least one readout unit is at least partially embedded in the embedding material of the electronic unit.

3. The detector module of claim 1, further comprising:
   a control circuit configured to control the at least one readout unit and/or the radio.

4. The detector module of claim 3, wherein the control circuit is at least partially embedded in the embedding material of the electronic unit.

5. The detector module of claim 1, wherein the radio module has at least one radio antenna, and
   wherein the at least one radio antenna comprises a wire applied to a surface of the embedding material of the electronic unit or to a surface of the radio circuit.

6. The detector module of claim 5, further comprising:
   a control circuit configured to control the at least one readout unit and/or the radio module.

7. The detector module of claim 6, wherein the control circuit is at least partially embedded in the embedding material of the electronic unit.

8. The detector module of claim 1, wherein the electronic unit is manufactured using a fan-out wafer-level packaging or panel-level packaging method.

9. The detector module of claim 1, wherein the at least one electrically conductive connection is integrated in the electronic unit or applied to the embedding material of the electronic unit.

10. The detector module of claim 1, wherein the electronic unit is arranged in the stack arrangement between the sensor and the at least one readout unit.

11. The detector module of claim 1, wherein the sensor is configured as a direct-conversion sensor or a scintillator element and at least one photodiode array.

12. An X-ray detector comprising:

a plurality of detector modules, wherein each detector module comprises:

a sensor configured to convert incoming X-rays into electrical signals;

at least one readout unit configured to read out the electrical signals from the sensor;

a radio having a radio circuit, wherein the radio is configured to transmit the readout electrical signals by a wireless data transmission method; and an electronic unit arranged in a stacked arrangement with respect to the sensor, wherein the electronic unit comprises at least one electrically conductive connection for forwarding the readout electrical signals from the at least one readout unit to the radio, wherein the radio circuit of the radio is at least partially embedded in an embedding material of the electronic unit, wherein the electronic unit has a protruding surface area that protrudes in a direction perpendicular to a stacking direction beyond a planar extension of the sensor, and wherein the radio is arranged in the protruding surface area.

13. A medical imaging device comprising:

an X-ray detector; and an X-ray source arranged in opposition to the X-ray detector, wherein the X-ray detector is configured to: convert incoming X-rays into electrical signals; and read out the electrical signals, and wherein the X-ray detector comprises:

a radio having a radio circuit, wherein the radio is configured to transmit the readout electrical signals by a wireless data transmission method; and an electronic unit comprising at least one electrically conductive connection for forwarding the readout electrical signals to the radio, wherein the radio circuit of the radio is at least partially embedded in an embedding material of the electronic unit, wherein the medical imaging device is configured as a computed tomography device, wherein at least one detector module of the X-ray detector is arranged on a rotating part of the computed tomography device and a plurality of receiver units is arranged on a stationary part of the computed tomography device, wherein the plurality of receiver units is configured to, with the radio, provide a wireless data transmission, and wherein receiver units of the plurality of receiver units are arranged spaced apart from each other on the stationary part radially about an axis of rotation of the computed tomography device or as a group on the stationary part of the computed tomography device.

* * * * *